United States Patent
Boström et al.

[11] Patent Number: 5,807,339
[45] Date of Patent: Sep. 15, 1998

[54] STYLET UNIT FOR STIFFENING A HOLLOW, FLEXIBLE, ELONGATED COMPONENT

[75] Inventors: Mats Boström, Sundyberg; Ulf Lindegren, Enskede, both of Sweden

[73] Assignee: Pacesetter AB, Solna, Sweden

[21] Appl. No.: 758,521

[22] Filed: Nov. 29, 1996

[30] Foreign Application Priority Data

Dec. 4, 1995 [SE] Sweden ................ 9504334-5

[51] Int. Cl.$^6$ ................ A61M 5/178
[52] U.S. Cl. .............. 604/164; 604/281
[58] Field of Search ............ 128/639, 772; 604/280, 281, 282, 164, 264

[56] References Cited

U.S. PATENT DOCUMENTS

| | | | |
|---|---|---|---|
| 3,757,768 | 9/1973 | Kline | 604/170 X |
| 4,136,703 | 1/1979 | Wittkampf . | |
| 4,643,716 | 2/1987 | Drach | 604/281 X |
| 5,109,830 | 5/1992 | Cho | 128/772 |
| 5,125,395 | 6/1992 | Adair | 128/772 X |
| 5,131,406 | 7/1992 | Kaltenbach | 128/772 |
| 5,170,787 | 12/1992 | Lindegren . | |
| 5,179,961 | 1/1993 | Littleford | 128/772 |

FOREIGN PATENT DOCUMENTS

| | | |
|---|---|---|
| 0 381 810 | 8/1990 | European Pat. Off. . |
| WO 95/13111 | 5/1995 | WIPO . |

*Primary Examiner*—Wynn Wood Coggins
*Assistant Examiner*—A. T. Nguyen
*Attorney, Agent, or Firm*—Hill & Simpson

[57] ABSTRACT

A stylet unit which can be introduced into a narrow, hollow, flexible component, such as a hollow electrode cable for a heart stimulator, to stiffen the component and bend its distal end section, is in the form of a double stylet combination with a flexible stylet shell and an internal stylet, movably arranged inside the shell, with a pre-curved distal end section, whose radius of curvature is on a first side of the stylet. In an area before the pre-curved end section, the stylet has a pre-shaped stylet section with a pre-shaped stylet section whose radius of curvature is on the side of the stylet opposite the first side on which the end section's radius of curvature lies.

9 Claims, 1 Drawing Sheet

STYLET UNIT FOR STIFFENING A HOLLOW, FLEXIBLE, ELONGATED COMPONENT

BACKGROUND OF THE INVENTION

1. Field of the Invention

The present invention relates to a stylet unit which can be introduced into a flexible component, such as a hollow electrode cable for a heart stimulator, a catheter or some other tubular instrument, with a narrow, longitudinal internal channel, to stiffen the flexible component and to bend a distal end section of that component. More particularly, the invention relates to a stylet unit in the form of a double-stylet combination having a flexible, tubular stylet shell and an internal stylet, movably arranged inside the shell's channel, with a pre-curved distal end section which can be set to a retracted position inside the stylet shell or to an exposed, projecting position outside the shell and having a curvature to one side of the stylet.

A channeled component of the aforementioned kind could e.g. be a tubular conductor used for stimulation in the human body. Such a channeled component could be devised to serve either as an implant or for removal from the body after a medical treatment has been performed.

2. Description of the Prior Art

A stylet unit of the above general type is especially suitable for stiffening and guiding a hollow electrode cable for a heart stimulator during advancement of the electrode cable into a human heart and for anchoring a contact electrode (electrode head) at the distal end of the cable in a cavity of the heart. The introduction of such an electrode cable into the heart is usually through a suitable vein, and the contact electrode can be anchored in the right ventricle or atrium. The temporarily introduced stylet unit inside the hollow electrode cable extends through the cable's central channel from the cable's proximal end (which is subsequently connected to the heart stimulator) to its distal end on which the contact electrode is located.

A stylet unit is especially suitable for anchoring a contact electrode in the heart's atrium, so an appropriate J-shape can be imparted to the distal end section of the electrode cable, thereby facilitating introduction of the end section into the atrial auricle and anchoring the contact electrode in the trabeculae of the atrial auricle. After the contact electrode has been anchored at the desired site in the heart, the stylet unit is completely removed from the heart.

U.S. Pat. No. 5,170,787 describes (see FIG. 2 thereof) a stylet unit, in the form of a double stylet combination with a flexible, tubular shell containing a moveable internal stylet in the shell's central channel. At the proximal end of this known stylet unit, there is a maneuvering handle with which the shell and the internal stylet can be moved in relation to each other to retract the stylet's pre-curved distal end section into the surrounding shell's distal end section, or to deploy the pre-curved distal end section of the stylet outside the opening of the shell's end section into the central channel of the distal end section of the surrounding electrode cable in order to impart the desired curved shape to the distal end section.

U.S. Pat. No. 4,136,703 shows another example of a stylet unit, devised as a double stylet combination, for an electrode cable. The stylet unit contains a pre-curved internal stylet in its distal end section.

These known types of stylet units described in the aforementioned documents, i.e. double stylet combinations, are incapable of insuring that the stylet unit—and accordingly its surrounding electrode cable—attains a desired, substantially straight conformation when the internal stylet's pre-curved distal end section is retracted into the corresponding distal end section of the stylet shell.

SUMMARY OF THE INVENTION

An object of the present invention is to provide an improved type of stylet unit with which it is possible to attain a much straighter, i.e. with less lateral bending, and much better shape for the distal end section of the stylet shell, with a stylet unit devised as a double stylet combination, when the pre-curved distal end section of the movable internal stylet has been fully retracted into the shell's channel and is surrounded by the stylet shell's enclosing distal end section.

A further object of the invention is to provide a stylet unit wherein, when the stylet's pre-curved distal end section has been exposed and deployed outside the opening of the stylet shell, it produces the desired bending of a corresponding section of the narrow, channel equipped flexible component, which (as noted above) could be a hollow cable, a catheter or some other kind of elongate instrument posing some resistance to bending.

An additional object of the invention is to provide a stylet unit whose internal stylet has a very pronounced J or fish hook shape at its distal end section when this section is fully deployed outside the distal end section of the stylet shell.

The above objects are achieved in accordance with the principles of the present invention in a stylet unit in the form of a double stylet combination, having an internal stylet freely movable within a longitudinal channel of a stylet shell, wherein the internal stylet has a pre-curved distal end section, having a radius of curvature on a first side of the internal stylet, the pre-curved distal end section being deployable from a retracted position inside the stylet shell to an exposed position projecting from the stylet shell, and wherein the internal stylet has a pre-shaped section preceding the aforementioned distal end section, the pre-shaped section having a curve with a radius of curvature on a side of the internal stylet other than the aforementioned first side.

A major distinctive feature of the stylet unit according to the invention is that in the stylet area located immediately before (in a direction from the stylet unit's proximal end to its distal end) the pre-curved distal end section, the internal stylet is provided with a pre-shaped stylet section having a radius of curvature located on the opposite side of the stylet in relation to the first side of the stylet.

As a result of this combination of two diametrically opposed, pre-shaped curved stylet sections on the internal stylet in accordance with the invention, the distal end section of the stylet shell of the stylet unit has a very stretched or flat S-shape when the internal stylet's double-bend end section has been completely retracted into the distal end section of a stylet shell.

With a stylet unit devised in this manner, the shape of the distal section of the stylet shell has an undulating shape which is so flat that when the "double-bend" end section of the stylet is fully retracted into shell, the maximum deviation from the midline of the shell's otherwise straight section becomes far less than with a conventional stylet design only utilizing a distal end section with pre-bending on one side.

For the shape of the stylet shell to be as straight as possible, when the internal stylet is fully retracted into the shell, it would also be appropriate for the part of the internal stylet between the stylet's proximal end section and the stylet's pre-shaped stylet section, as well as the pre-shaped distal end section, to have a substantially straight configuration in the unloaded state.

It would be desirable for the internal stylet's pre-shaped stylet section and the stylet's pre-curved distal end section to lie on the same side of the substantially straight section of the stylet's longitudinal axis. Here, the centers of curvature for the stylet's pre-shaped stylet sections and the stylet's pre-curved distal end section can then lie either on the same side of the said longitudinal axis or on opposite sides of this longitudinal axis. An optimally flat or longitudinally undulating S-shape for the stylet shell, with the inner stylet retracted therein, is achieved when the stylet's pre-shaped stylet section and the stylet's pre-curved distal end section are in a common plane which then preferably encompasses the rest of the stylet with a substantially straight configuration.

The stylet's pre-curved distal end section is suitably designed and arranged, in relation to the straight part of the stylet, between the stylet's proximal end and the pre-shaped stylet section, so this straight section of the stylet's longitudinal axis borders the hook-like, pre-curved distal end section.

DESCRIPTION OF THE PREFERRED EMBODIMENTS

Figure 1:
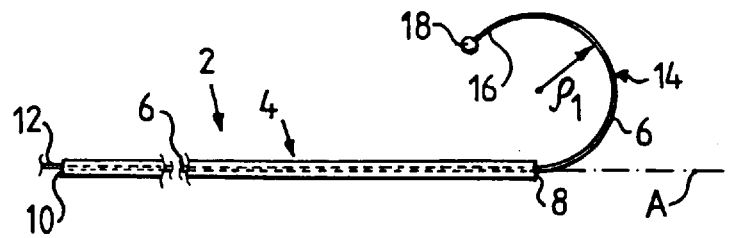
FIG. 1 schematically shows the relevant parts of a conventional stylet unit in which the internal stylet's pre-curved distal end section projects outside the stylet shell's opening.
Figure 2:
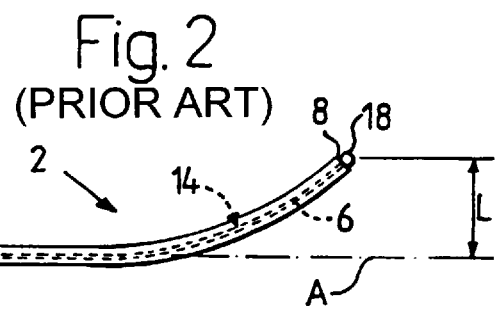
FIG. 2 shows the stylet unit, depicted in FIG. 1, when the stylet's pre-curved distal end section has been retracted into the tubular stylet shell's distal end section.

FIGS. 1 and 2 schematically show the distal end area of a known stylet unit 2, which is a double stylet combination consisting of a flexible, tubular stylet shell 4 with a freely moving stylet 6 inside the channel of the shell 4. The distal end of the stylet shell 4 is designated 8, the shell's proximal end is designated 10 and the stylet's 6 proximal end is designated 12. As FIG. 1 shows, the internal stylet 6 has a pre-curved distal end section 14 which, in this case, is generally semicircular with a radius of curvature $e_1$ and a short, straight stylet end section 16 with a end stop ball 18 which prevents the end section 14 from being unintentionally drawn too far into the stylet shell 4 and minimizes the risk of penetration by the stylet end section 16 (not shown here) into the surrounding electrode cable wall.

When the stylet unit 2 has been introduced into a longitudinally hollow electrode cable (not shown), the pre-curved distal end section 14 serves to impart a curved, J-shape to the end section of the electrode cable.

The stylet unit is shown in FIG. 2 as it might appear when the pre-curved distal section 14 of the internal stylet 6 is completely retracted into the end section of the stylet shell 4, so the stop ball 18 presses against the opening on the distal end 8 of the tubular stylet shell. With the "single-bend" version of the stylet's distal end section 14, as shown in FIG. 1, a bend is produced in the end section of the stylet shell 4 when the end section 14 is fully retracted. This means that the shell end 8 assumes a position corresponding to a lateral deviation L from the longitudinal axis A of the straight section of the stylet unit 2, shown to the left in FIGS. 1 and 2.

The relative movement required between the shell 4 and the stylet 6 to deploy or retract the end section 14 into/out of the stylet shell 4 is usually achieved with a maneuvering and holding implement (not shown) arranged at the proximal end 10 of the shell 4. Here, the implement could be a holding device, for example, connected to the stylet shell 4, and a gripping device (handle), capable of moving the stylet in relation to the shell when the holding device is kept still. Alternatively, movement between the internal stylet 6 and the surrounding shell 4 could be achieved by holding the stylet 6 while still moving the shell 4.

Figure 3:
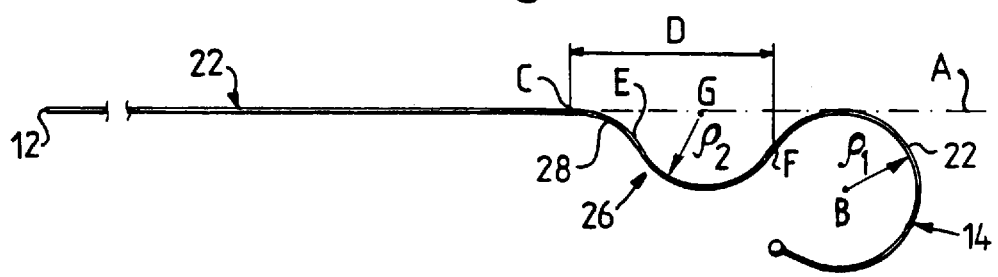
FIG. 3 shows the internal stylet for a stylet unit, depicted in FIG. 4, according to the invention.
Figure 4:
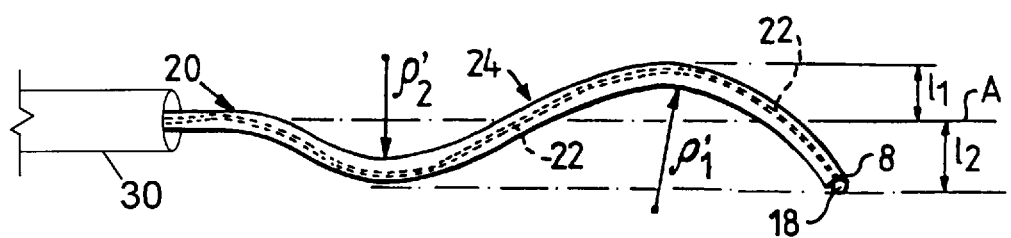
FIG. 4 shows a stylet unit according to the invention when the stylet's pre-curved distal end section has been completely retracted into the stylet shell.

FIGS. 3 and 4 show a internal stylet and a stylet unit according to the invention.

The stylet unit, devised as a double stylet combination, according to the invention is generally designated 20, whereas the movably arranged internal stylet in the shell's channel is designated 22. This internal stylet 22 is shown in FIG. 3 in a completely unloaded state, i.e. before the stylet has been retracted into the tubular stylet shell 24 of the stylet unit 20. As shown in FIG. 3, the internal stylet 22 has a pre-curved distal end section 14 of a known kind (cf. FIG. 1). This pre-curved semicircular end section 14 has a radius of curvature $e_1$ whose center of curvature B lies on the underside of the longitudinal axis A of the straight stylet section between point C and the stylet's proximal end 12. A distinguishing feature of the stylet according to the invention is that the stylet—over an area D—has a pre-shaped stylet section formed by a pre-curved stylet section 26 with a radius of curvature $P_2$ and a semicircular transition section 28 between point E and point C. The pre-curved stylet section 26 extends from point E to the flexion point F where the pre-curved distal end section 14 of the stylet 22 begins.

As shown in FIG. 3, radius of curvature of the stylet section 26 is $P_2$ (from the center of curvature G) located on one side of the stylet 22, opposite the side where the radius of the curvature $P_1$ of the pre-curved distal end section 14 is located. Viewed along the longitudinal axis of the stylet 22 from its proximal end 12, via points C, E and F, to the stop ball 18, radius of curvature $P_1$ of the stylet section 26 is on the stylet's right side, in the drawing plane of FIG. 3.

As FIG. 3 also shows, the pre-shaped stylet section of the stylet 22 and its pre-curved distal end section 14 are on the same side of the longitudinal axis A as the straight section of the internal stylet 22 located between the proximal end 12 and the point C.

In the embodiment shown in FIG. 3, the center G of the radius of curvature's $P_2$ is on the longitudinal axis A, whereas the center B of the radius of curvature lies below the longitudinal axis. The pre-curved stylet section 26, however, could be devised so the centers G and B are on opposite sides of the longitudinal axis A.

Finally, FIG. 4 shows how the tubular stylet shell 24 in the unloaded state is bent laterally by the pre-curved stylet section 26 of the internal stylet 22 and by the pre-curved distal end section 14 when the two pre-curved parts of the stylet have been completely retracted into the tubular stylet shell 24. This causes the stop ball 18 to press against the opening of the shell's channel at the distal end 8 of the shell. In practice, retraction of the end section 14 and the stylet section 26 into the shell 24 is achieved by sliding the shell over both parts of the stylet. The stylet shell 24 acquires a greatly flattened S-shape with two areas, curving in opposite directions, at the shell's distal end section, viz. a concluding curved section with a radius of curvature $P'_1$ and a section before this, curved in the opposite direction $P'_2$. The radius of curvature $P'_1$ of the shell 24, is mainly caused by the radius of curvature $P_1$ of the pre-curved end section 14 whereas the radius of curvature $P'_2$ of the shell 24 is mainly caused by the radius of curvature $P_2$ of the pre-curved stylet section 26.

The wavy, double-bend distal end area of the stylet shell 24 will, as a result of the special configuration stylet 22, display maximum lateral bending $I_1$ and $I_2$, seen from the stylet unit's longitudinal axis A. Both the deviation $I_1$ and the deviation $I_2$ will be much less than the lateral deviation L (see FIG. 2) obtained with the use of a stylet shell 4 of the same kind as the stylet shell 24 used with the conventional type of internal stylet 6, according to FIG. 1. Even if the sum of the deviations $I_1$ and $I_2$ were as large as the lateral deviation L, according to FIG. 2, a maximum deviation from the longitudinal axis A, which is much less than the deviation L obtained with the known technique according to FIGS. 1 and 2. The deviation-reducing effect attained according to the invention is because the lateral deviations 11 and 12 are respectively located on opposite side of the center of longitudinal axis A.

As the above shows, the stylet unit according to the invention is especially suitable for achieving a stiffening of an electrode cable 30 during the cable's advancement through a vein to a patient's heart with the introduction being concluded by bending a distal end section of the cable. During the electrode cable's advancement through a vein, it would obviously be advantageous for the electrode cable 30 to be as straight as possible. This means, in turn, that the employed stylet unit must be as straight as possible during advancement, since it is the stylet unit which gives the electrode cable 30 its stiffness. A stylet unit according to FIG. 4 will greatly simplify introduction of an electrode cable 30 by a physician into a patient's heart, compared to the use of a conventional stylet unit (according to FIG. 2) which imparts much greater lateral bending than the double stylet type of curved stylet unit, shown in FIG. 4, according to the present invention.

Although modifications and changes may be suggested by those skilled in the art, it is the intention of the inventors to embody within the patent warranted hereon all changes and modifications as reasonably and properly come within the scope of their contribution to the art.

We claim as our invention:

1. A stylet unit and component combination comprising:
    a flexible, tubular stylet shell having an internal longitudinal channel therein;
    an internal stylet having a pre-curved distal end section, said internal stylet being slideable within said channel between a retracted position wherein said distal end section is completely contained within said shell and a deployed position wherein said distal end section projects from said shell, said distal end section having a radius of curvature on a first side of said stylet and said stylet having a pre-shaped stylet section preceding said distal end section having a curve with a radius of curvature disposed on an opposite side of said stylet from said first side; and
    a hollow, flexible elongated component having a first end section into which the stylet unit is removably introducible for stiffening the component and to bend a second end section of the component, opposite said first end section.

2. A stylet unit and component combination as claimed in claim 1 wherein said internal stylet has a proximal end, a distal end disposed at an end of said distal end section and a longitudinal axis extending between said distal end and said proximal end, and a substantially straight section disposed between said proximal end and said pre-shaped section, said substantially straight section, said pre-shaped section and said distal end section all having a substantially straight configuration along said longitudinal axis when said internal stylet is in said retracted position.

3. A stylet unit and component combination as claimed in claim 2 wherein said pre-shaped section and said distal end section are disposed on a same side of the longitudinal axis in said substantially straight section.

4. A stylet unit and component combination as claimed in claim 3 wherein said pre-shaped end section and said distal end section each has a radius of curvature, and wherein said radius of curvature of said pre-shaped section and said radius of curvature of said distal end section are on a same side of said longitudinal axis.

5. A stylet unit and component combination as claimed in claim 3 wherein said pre-shaped end section and said distal end section each has a radius of curvature, and wherein said radius of curvature of said pre-shaped section and said radius of curvature of said distal end section are on different sides of said longitudinal axis.

6. A stylet unit and component combination as claimed in claim 3 wherein said substantially straight section, said pre-shaped section and said distal end section are disposed adjacent to each other in sequence from said proximal end to said distal end of said internal stylet.

7. A stylet unit and component combination as claimed in claim 2 wherein said pre-shaped section and said distal end section are disposed in a common plane.

8. A stylet unit and component combination as claimed in claim 7 wherein said common plane contains said substantially straight section.

9. A stylet unit and component combination as claimed in claim 1 wherein said pre-shaped end section and said distal end section each has a radius of curvature, and wherein said radius of curvature of said pre-shaped section is substantially constant within said pre-shaped section and wherein said radius of curvature of said distal end section is substantially constant within said distal end section.

* * * * *